(12) United States Patent
Lai et al.

(10) Patent No.: US 9,343,687 B1
(45) Date of Patent: May 17, 2016

(54) IMIDAZO[1,2-A]PYRIMIDINE-CONTAINING COMPOUNDS, METHOD FOR PREPARING THE SAME, AND THEIR USE IN ELECTRONIC DEVICES

(71) Applicant: National Chi Nan University, Puli, Nantou (TW)

(72) Inventors: Long-Li Lai, Taichung (TW); Pei-An Hsieh, Nantou (TW); Yan-Chih Lu, Nantou (TW)

(73) Assignee: NATIONAL CHI NAN UNIVERSITY, Puli, Nantou (TW)

( * ) Notice: Subject to any disclaimer, the term of this patent is extended or adjusted under 35 U.S.C. 154(b) by 0 days.

(21) Appl. No.: 14/745,968

(22) Filed: Jun. 22, 2015

(30) Foreign Application Priority Data

Dec. 10, 2014 (TW) .............................. 103143001 A

(51) Int. Cl.
| | | |
|---|---|---|
| *C07D 487/04* | (2006.01) | |
| *H01L 51/00* | (2006.01) | |
| *C09K 11/06* | (2006.01) | |
| *H01L 51/50* | (2006.01) | |

(52) U.S. Cl.
CPC .......... *H01L 51/0072* (2013.01); *C07D 487/04* (2013.01); *C09K 11/06* (2013.01); *H01L 51/5012* (2013.01); *C09K 2211/1007* (2013.01); *C09K 2211/1011* (2013.01); *C09K 2211/1044* (2013.01)

(58) Field of Classification Search
CPC .................................................. C07D 487/04
See application file for complete search history.

(56) References Cited

FOREIGN PATENT DOCUMENTS

| KR | 20120078530 A | 7/2012 | |
| KR | 20120078530 | * 10/2012 | ............. C09K 11/06 |

\* cited by examiner

*Primary Examiner* — Erich A Leeser
(74) *Attorney, Agent, or Firm* — Merchant & Gould P.C.

(57) ABSTRACT

The present disclosure describes novel imidazo[1,2-a]pyrimidine-containing organic light-emitting compounds represented by formula (I):

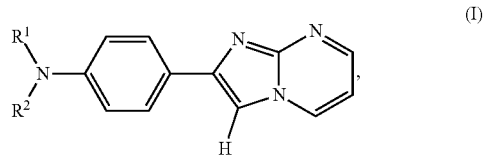

wherein
$R^1$ and $R^2$ independently represent hydrogen, an alkyl group, or an aryl group which is unsubstituted or substituted with at least one substituent selected from the group consisting of an alkyl group, an alkoxy group, and a halo group with the proviso that at least one of $R^1$ and $R^2$ is the aryl group. The disclosure further relates to methods for preparing these compounds, to electronic devices comprising the same, and to the use of the compounds as OLED material.

14 Claims, 9 Drawing Sheets

IMIDAZO[1,2-A]PYRIMIDINE-CONTAINING COMPOUNDS, METHOD FOR PREPARING THE SAME, AND THEIR USE IN ELECTRONIC DEVICES

CROSS-REFERENCE TO RELATED APPLICATION

This application claims priority to and the benefit of Taiwanese Application No. 103143001, filed Dec. 10, 2014, the entire disclosure of which is incorporated herein by reference.

FIELD

This disclosure relates, inter alia, to imidazo[1,2-a]pyrimidine-containing compounds, to methods for preparing these compounds, and to electronic devices comprising these compounds.

BACKGROUND

A key focus of the research and development in the field of organic light-emitting diodes (OLEDs) is to develop more high-performance light-emitting materials capable of emitting blue fluorescent light under photoluminescence or electroluminescence excitation. For example, KP20120078530 discloses a series of organic light-emitting compounds based on formula (1) for a light-emitting layer of an OLED:

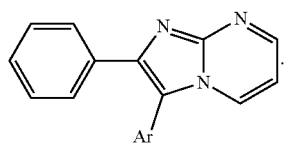

(1)

The disclosed compounds possess good fluorescence quantum efficiency; however, the color purity of the blue fluorescent light emitted therefrom is inferior. Moreover, the compound has a relatively large molecular weight, so that a relatively high gasification temperature is required for gasifying the organic light-emitting compound in the process of forming a light-emitting layer from the organic light-emitting compound.

There is thus a need in the art for an organic light-emitting compound which may emit blue fluorescent light having a superior color purity after being excited by light or electricity.

SUMMARY

Therefore, a first object of this disclosure is to provide an imidazo[1,2-a]pyrimidine-containing organic light-emitting compound which may emit blue fluorescent light having a superior color purity after being excited by light or electricity.

A second object of this disclosure is to provide an electronic device with a light-emitting layer including the imidazo[1,2-a]pyrimidine-containing compound.

A third object of this disclosure is to provide a method for preparing the imidazo[1,2-a]pyrimidine-containing compound.

According to the first aspect of this disclosure, there is provided an imidazo[1,2-a]pyrimidine-containing compound represented by formula (I):

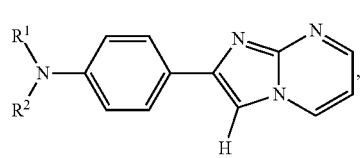

(I)

wherein $R^1$ and $R^2$ independently represent hydrogen, an alkyl group, or an aryl group which is unsubstituted or substituted with at least one substituent selected from the group consisting of an alkyl group, an alkoxy group, and a halo group with the proviso that at least one of $R^1$ and $R^2$ is said aryl group.

According to the second aspect of this disclosure, there is provided an electronic device with a light-emitting layer including the compound represented by formula (I).

According to the third aspect of this disclosure, there is provided a method for preparing the compound represented by formula (I). The method comprises subjecting a compound of formula (II) to an amination reaction with a compound of formula (III),

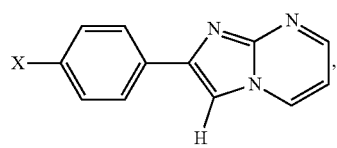

(II)

wherein X represents I, Br, F, or Cl,

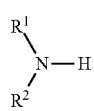

(III)

wherein $R^1$ and $R^2$ independently represent hydrogen, an alkyl group, or an aryl group which is unsubstituted or substituted with at least one substituent selected from the group consisting of an alkyl group, an alkoxy group, and a halo group with the proviso that at least one of $R^1$ and $R^2$ is said aryl group.

BRIEF DESCRIPTION OF THE DRAWINGS

Other features and advantages of this disclosure will become apparent in the following detailed description of the embodiments with reference to the accompanying drawings, of which.

DETAILED DESCRIPTION

Figure 1:
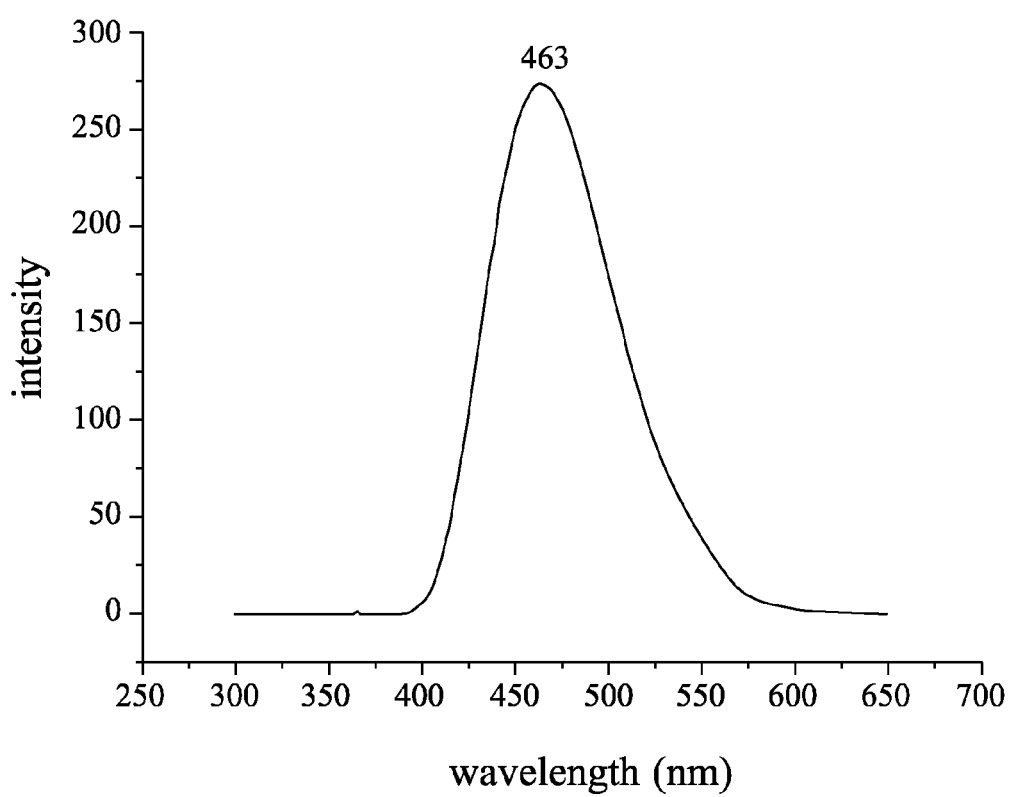
FIGS. 1 to 9 respectively illustrate the corresponding fluorescent spectra of the imidazo[1,2-a]pyrimidine-containing organic light-emitting compounds in Examples 1-9.

An imidazo[1,2-a]pyrimidine-containing compound according to this disclosure is represented by formula (I):

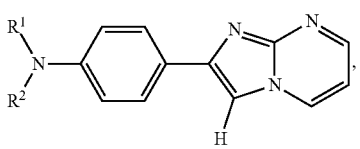

(I)

wherein

R¹ and R² independently represent hydrogen, an alkyl group, or an aryl group which is unsubstituted or substituted with at least one substituent selected from the group consisting of an alkyl group, an alkoxy group, and a halo group with the proviso that at least one of R¹ and R² is said aryl group.

Preferably, the aryl group is selected from the group consisting of:

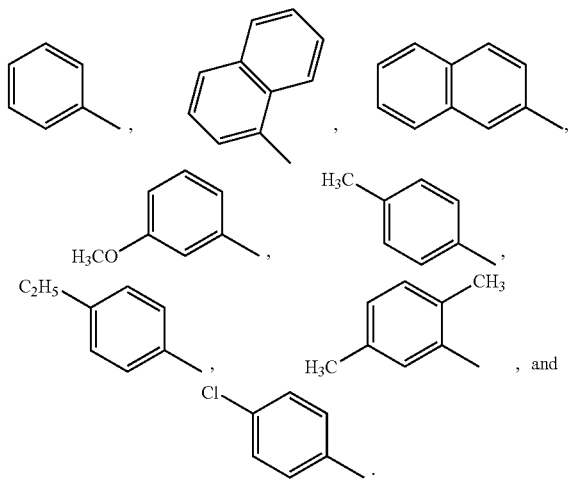

Preferably, both R¹ and R² independently represent the aryl group. More preferably, R¹ and R² are independently selected from the group consisting of

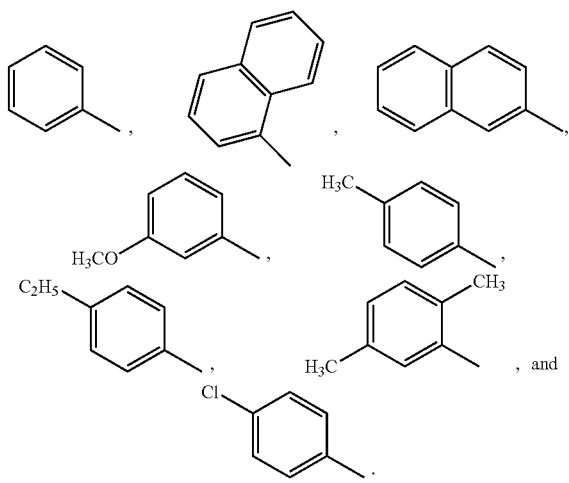

Preferably, the alkyl group contains from 1 to 25 carbon atoms. More preferably, the alkyl group contains from 1 to 10 carbon atoms. Most preferably, the alkyl group contains from 1 to 5 carbon atoms.

The imidazo[1,2-a]pyrimidine-containing compound according to this disclosure emits blue fluorescent light having a wavelength ranging preferably from 430 to 480 nm under photoluminescence or electroluminescence excitation.

The imidazo[1,2-a]pyrimidine-containing compound according to this disclosure may be used as a light-emitting layer of an electronic device.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., Nature Photonics 2008, 1-4), but preferably organic electroluminescent devices (OLEDs, PLEDs), particularly preferably fluorescent OLEDs.

A method for preparing the imidazo[1,2-a]pyrimidine-containing compound represented by formula (I) according to this disclosure comprises subjecting a compound of formula (II) to an amination reaction with a compound of formula (III),

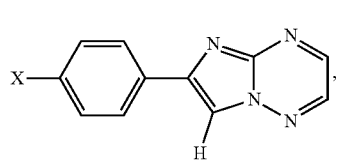

(II)

wherein X represents I, Br, F, or Cl,

(III)

wherein R¹ and R² independently represent hydrogen, an alkyl group, or an aryl group which is unsubstituted or substituted with at least one substituent selected from the group consisting of an alkyl group, an alkoxy group, and a halo group with the proviso that at least one of R¹ and R² is the aryl group.

Preferably, the amination reaction is performed in the presence of a catalyst, a solvent, and optionally, an alkaline compound at a temperature ranging from 110° C. to 130° C.

There is no limitation on the catalyst used as long as the catalyst may enhance the amination reaction. Examples of catalysts suitable for the amination reaction include, but are not limited to, palladium(II) acetate(Pd(OAc)$_2$) and tri-tert-butylphosphine (P(t-Bu)$_3$).

Preferably, the alkaline compound is cesium carbonate (Cs$_2$CO$_3$).

There is no limitation on the solvent used as long as the solvent may dissolve the compound of formula (II), the compound of formula (III), the catalyst, and the alkaline compound or the solvent may permit the amination reaction to take place in a homogeneous phase. Examples of solvents suitable for the amination reaction include, but are not limited to, toluene and N-methylpyrrolidone (NMP).

The following examples are provided to illustrate the embodiments of this disclosure, and should not be construed as limiting the scope of the disclosure.

EXAMPLES

Preparation of Starting Material 2-aminopyrimidine (10.5 g, 110 mmol) and 2,4'-dibromoacetophenone (27.8 g, 100 mmol) were dissolved in ethanol (350 ml) to form a mixture. The mixture was slowly heated from 25° C. to 75° C. and was refluxed at 75° C. for 4 hours. The mixture was then cooled to 25° C., and potassium hydroxide (2 equiv.) was added thereto while stirring to precipitate a significant amount of a solid. The solid was separated via filtration, and a mixture of dichloromethane and n-hexane (1:10) was added thereto to conduct recrystallizaiton. Compound 1 was obtained as a colorless solid (15.4 g, 56% yield): $^1$H-NMR: (300 MHz, DMSO), δ (ppm): 7.08 (dd, J=4.2, 6.6, 1H, 1×Ar—H), 7.67 (d, J=8.4, 2H, 2×Ar—H), 7.96 (d, J=8.4, 2H, 2×Ar—H), 8.43 (s, 1H, 1×Ar—H), 8.54-8.56 (m, 1H, 1×Ar—H), 8.96 (dd, J=4.8, 6.6, 1H, 1×Ar—H); MALDI-TOF MS: m/z 274.12 [M+H]$^+$. Compound 1 was confirmed to have the following structure:

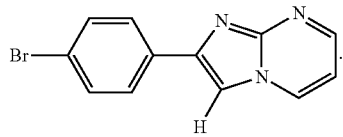 [SMILES: Brc1ccc(-c2cn3cccnc3n2)cc1]

Example 1

Preparation of an imidazo[1,2-a]pyrimidine-containing Compound

Step (A)

Compound 1 (0.27 g, 1.0 mmol) was dissolved in a mixture of anhydrous toluene (9 ml) and N-methylpyrrolidone (1 ml) contained in a reaction vessel, followed by adding sequentially palladium acetate (0.04 g, 0.18 mmol), tri-t-butyl phosphine (97 μl, 0.41 mmol), diphenylamine (0.25 g, 1.5 mmol), and cesium carbonate (0.52 g, 1.6 mmol) to give a reaction mixture. The reaction mixture was refluxed for 90 minutes under a nitrogen atmosphere in a microwave device (130° C., 400 W) to give a coarse mixture.

Step (B)

The coarse mixture obtained in Step (A) was purified by column chromatography (silica powders, tetrahydrofuran/n-hexane (3:1) as eluent). A filtrate was collected and concentrated under reduced pressure to remove the eluent. A light tawny solid (0.025 g, 6.9% yield) was obtained: $^1$H-NMR: (300 MHz, DMSO), δ (ppm): 7.10-7.03 (m, 9H, 9×Ar—H), 7.34 (t, J=7.5, 4H, 4×Ar—H), 7.91 (d, J=8.4, 2H, 2×Ar—H), 8.28 (s, 1H, 1H, 1×Ar—H), 8.49 (d, J=1.5, 1H, 1×Ar—H), 8.94 (d, J=5.4, 1H, 1×Ar—H); MALDI-TOF MS: m/z 362.07 [M+H]$^+$. The light tawny solid was confirmed to have the following structure:

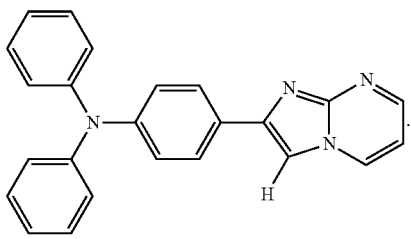 [SMILES: c1ccc(N(c2ccccc2)c2ccc(-c3cn4cccnc4n3)cc2)cc1]

Example 2

Preparation of an imidazo[1,2-a]pyrimidine-containing Compound

The procedure of Example 1 was repeated except that diphenylamine (0.25 g, 1.5 mmol) used in step (A) of Example 1 was replaced with N-phenyl-1-naphthylamine (0.33 g, 1.5 mmol) to give a light tawny solid (0.033 g, 8.0% yield): $^1$H-NMR: (300 MHz, DMSO), δ(ppm): 7.04-6.93 (m, 6H, 6×Ar—H), 7.27 (t, J=7.8, 2H, 2×Ar—H), 7.62-7.40 (m, 4H, 4×Ar—H), 7.86 (d, J=8.8, 3H, 3×Ar—H), 7.98 (d, J=8.1, 2H, 2×Ar—H), 8.22 (s, 1H, 1×Ar—H), 8.47 (d, J=1.9, 1H, 1×Ar—H), 8.92 (d, J=6.9, 1H, 1×Ar—H); MALDI-TOF MS: m/z 411.98 [M+H]$^+$. The light tawny solid was confirmed to have the following structure:

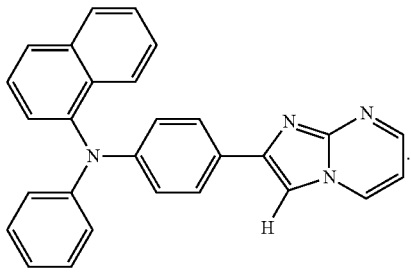 [SMILES: c1ccc(N(c2ccc(-c3cn4cccnc4n3)cc2)c2cccc3ccccc23)cc1]

Example 3

Preparation of an imidazo[1,2-a]pyrimidine-containing Compound

Step (A)

Compound 1 (0.55 g, 2.0 mmol) was dissolved in a mixture of anhydrous toluene (16 ml) and N-methylpyrrolidone (3 ml) contained in a reaction vessel, followed by adding sequentially palladium acetate (0.08 g, 0.36 mmol), tri-t-butylphosphine (0.19 ml 0.81 mmol), aniline (0.27 ml, 3.0 mmol), and cesium carbonate (0.72 g, 2.2 mmol) to give a reaction mixture. The reaction mixture was refluxed for 90 minutes under a nitrogen atmosphere in a microwave device (130° C., 100 W) to give a coarse mixture.

Step (B)

The coarse mixture obtained in Step (A) was concentrated under reduced pressure to remove toluene, followed by adding water into the reaction vessel to precipitate a solid, which was separated via filtration.

Step (C)

The solid obtained in Step (B) was purified by column chromatography (silica powders, tetrahydrofuran/n-hexane (3:1) as eluent). A filtrate was collected and concentrated under reduced pressure to remove the eluent. A light tawny solid (0.28 g, 48% yield) was obtained: $^1$H-NMR: (300 MHz, DMSO), δ(ppm): 6.87 (t, J=7.2, 1H, 1×Ar—H), 7.01 (dd, J=6.6, 4.2, 1H, 1×Ar—H), 7.16-7.12 (m, 4H, 4×Ar—H), 7.27 (t, J=7.6, 2H, 2×Ar—H), 7.87 (d, J=8.7, 2H, 2×Ar—H), 8.22 (s, 1H, 1×Ar—H), 8.40 (s, 1H, 1×N—H), 8.47 (dd, J=4.2, 1.8, 1H, 1×Ar—H), 8.92 (dd, J=6.9, 2.1, 1H, 1×Ar—H); MALDI-TOF MS: m/z 287.10 [M+H]$^+$. The light tawny solid was confirmed to have the following structure:

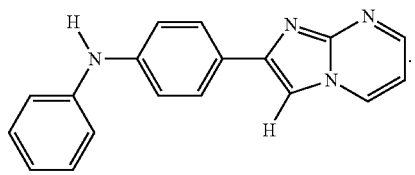 [SMILES: c1ccc(Nc2ccc(-c3cn4cccnc4n3)cc2)cc1]

Example 4

Preparation of an imidazo[1,2-a]pyrimidine-containing Compound

The procedure of Example 3 was repeated except that aniline (0.27 ml, 3.0 mmol) used in step (A) of Example 3 was replaced with 1-naphthylamine (0.43 g, 3.0 mmol) to give a light tawny solid (0.25 g, 37% yield): $^1$H-NMR: (300 MHz, DMSO), δ (ppm): 7.01 (dd, J=6.3, 4.2, 1H, 1×Ar—H), 7.11 (d, J=8.4, 1H, 1×Ar—H), 7.60-7.40 (m, 5H, 5×Ar—H), 7.93-7.85 (m, 3H, 3×Ar—H), 8.15-8.19 (m, 1H, 1×Ar—H), 8.21 (s, 1H, 1×N—H), 8.46 (d, J=4.2, 2H, 2×Ar—H), 8.92 (d, J=6.6, 1H, 1×Ar—H); MALDI-TOF MS: m/z 336.07 [M+H]$^+$. The tawny solid was confirmed to have the following structure:

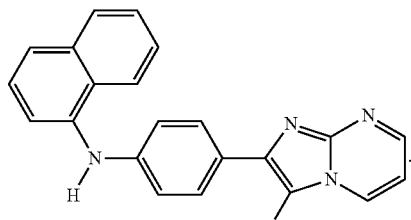

Example 5

Preparation of an imidazo[1,2-a]pyrimidine-containing Compound

The procedure of Example 3 was repeated except that aniline (0.27 ml, 3.0 mmol) used in step (A) of Example 3 was replaced with p-toluidine (0.32 g, 3.0 mmol) to give a light tawny solid (0.25 g, 37% yield): $^1$H-NMR: (300 MHz, DMSO), δ (ppm): 2.25 (s, 3H, 1×CH$_3$), 7.11-6.99 (m, 7H, 1×Ar—H), 7.83 (d, J=8.7, 2H, 2×Ar—H), 8.20 (s, 1H, 1×Ar—H), 8.25 (s, 1H, 1×N—H), 8.46 (dd, J=4.2, 1.8, 1H, 1×Ar—H), 8.91 (dd, J=6.9, 2.1, 1H, 1×Ar—H); MALDI-TOF MS: m/z 301.18 [M+H]$^+$. The light tawny solid was confirmed to have the following structure:

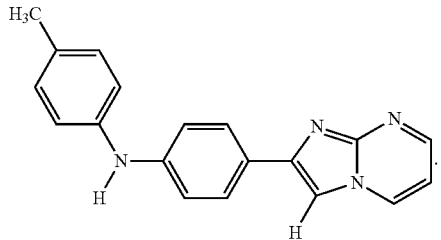 [SMILES: Cc1ccc(Nc2ccc(-c3cn4cccnc4n3)cc2)cc1]

Example 6

Preparation of an imidazo[1,2-a]pyrimidine-containing Compound

The procedure of Example 3 was repeated except that aniline (0.27 ml, 3.0 mmol) used in step (A) of Example 3 was replaced with m-anisidine (0.37 ml, 3.0 mmol) to give a light yellowish brown solid (0.27 g, 43% yield): $^1$H-NMR: (300 MHz, DMSO), δ(ppm): 3.73 (s, 3H, 1×CH$_3$), 6.45 (dd, J=8.1, 1.8, 1H, 1×Ar—H), 6.66 (s, 1H, 1×Ar—H), 6.72 (d, J=8.1, 1H, 1×Ar—H), 7.02 (dd, J=4.2, 6.6, 1H, 1×Ar—H), 7.17 (dd, J=7.8, 6.3, 3H, 3×Ar—H), 7.87 (d, J=8.4, 2H, 2×Ar—H), 8.22 (s, 1H, 1×Ar—H), 8.40 (s, 1H, 1×N—H), 8.47 (dd, J=3.9, 2.1, 1H, 1×Ar—H), 8.92 (t, J=6.6, 1H, 1×Ar—H); MALDI-TOF MS: m/z 317.00 [M+H]$^+$. The light yellowish brown solid was confirmed to have the following structure:

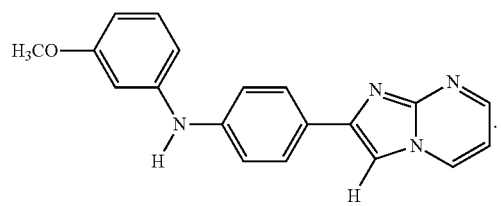 [SMILES: COc1cccc(Nc2ccc(-c3cn4cccnc4n3)cc2)c1]

Example 7

Preparation of an imidazo[1,2-a]pyrimidine-containing Compound

The procedure of Example 3 was repeated except that aniline (0.27 ml, 3.0 mmol) used in step (A) of Example 3 was replaced with 2,5-dimethylaniline (0.37 ml, 3.0 mmol) to give a light yellow solid (0.16 g, 25% yield): $^1$H-NMR: (300 MHz, DMSO), δ(ppm): 2.16 (s, 3H, 1×CH$_3$), 2.23 (s, 3H, 1×CH$_3$), 6.77 (d, J=7.5, 1H, 1×Ar—H), 6.92 (d, J=8.7, 2H, 2×Ar—H), 7.11-6.99 (m, 3H, 3×Ar—H), 7.60 (s, 1H, 1×N—H), 7.81 (d, J=8.7, 2H, 2×Ar—H), 8.18 (s, 1H, 1×Ar—H), 8.45 (dd, J=4.2, 1.8, 1H, 1×Ar—H), 8.90 (t, J=6.6, 1H, 1×Ar—H); MALDI-TOF MS: m/z 315.02 [M+H]$^+$. The light yellow solid was confirmed to have the following structure:

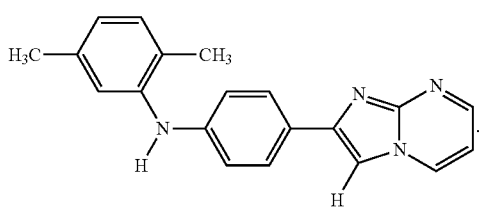 [SMILES: Cc1ccc(C)c(Nc2ccc(-c3cn4cccnc4n3)cc2)c1]

Example 8

Preparation of an imidazo[1,2-a]pyrimidine-containing Compound

The procedure of Example 3 was repeated except that aniline (0.27 ml, 3.0 mmol) used in step (A) of Example 3 was replaced with 4-ethylaniline (0.37 ml, 3.0 mmol) to give a light yellow solid (0.30 g, 48% yield): $^1$H-NMR: (300 MHz, DMSO), δ(ppm): 1.17 (t, J=7.5, 3H, 1×CH$_3$), 2.56 (quint, J=7.5, 2H, 1×CH$_2$), 7.01 (dd, J=6.6, 4.2, 1H, 1×Ar—H), 7.14-7.05 (m, 6H, 6×Ar—H), 7.84 (d, J=8.4, 2H, 2×Ar—H), 8.20 (s, 1H, 1×N—H), 8.27 (s, 1H, 1×Ar—H), 8.46 (dd, J=3.9, 1.8, 1H, 1×Ar—H), 8.91 (dd, J=6.6, 1.8, 1H, 1×Ar—H); MALDI-TOF MS: m/z 314.71 [M+H]$^+$. The light yellow solid was confirmed to have the following structure:

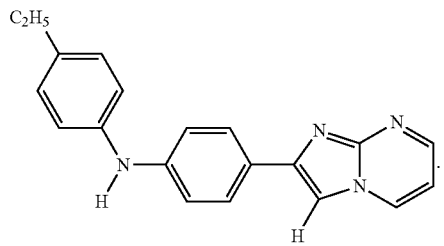 [SMILES: CCc1ccc(Nc2ccc(-c3cn4cccnc4n3)cc2)cc1]

Example 9

Preparation of an imidazo[1,2-a]pyrimidine-containing Compound

The procedure of Example 3 was repeated except that aniline (0.27 ml, 3.0 mmol) used in step (A) of Example 3 was replaced with 4-chloroaniline (0.38 g, 3.0 mmol) and that a mixture of tetrahydrofuran/n-hexane (2:1) was used as the eluent to give a light yellow solid (0.24 g, 37% yield): $^1$H-NMR: (300 MHz, DMSO), δ (ppm): 7.02 (dd, J=6.3, 4.5, 1H, 1×Ar—H), 7.14 (t, J=7.5, 4H, 4×Ar—H), 7.29 (d, J=8.4, 2H, 2×Ar—H), 7.89 (d, J=8.1, 2H, 2×Ar—H), 8.24 (s, 1H, 1×N—H), 8.48 (d, J=3.3, 1H, 1×Ar—H), 8.53 (s, 1H, 1×Ar—H), 8.93 (d, J=6.6, 1H, 1×Ar—H); MALDI-TOF MS: m/z 320.96 [M+H]$^+$. The light yellow solid was confirmed to have the following structure:

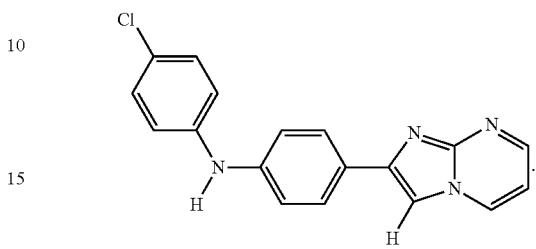

Physical Characteristics Test:

1. Maximum Absorption Wavelength (UV/Vis $\lambda_{max}$):

Each of the imidazo[1,2-a]pyrimidine-containing compounds in Examples 1-9 was dissolved in ethyl acetate to prepare a test solution having a concentration of 2×10$^{-4}$ M. The absorption spectrum of the test solution was measured using a Varian Carry 50 Bio US-Vis spectrophotometer in a wavelength range from 200 nm to 800 nm. The maximum absorption wavelength (UV/Vis $\lambda_{max}$, in nm) of each imidazo[1,2-a]pyrimidine-containing compound in Examples 1-9 was measured. The results are shown in Table 1.

2. Emission Wavelength (PL $\lambda_{max}$):

Each of the imidazo[1,2-a]pyrimidine-containing compounds in Examples 1-9 was dissolved in ethyl acetate to prepare a test solution having a concentration ranging from 1×10$^{-4}$ M to 1×10$^{-5}$ M. The test solution was measured using a Thermo Scientific Lumina fluorescence spectrometer under photoluminescence excitation of an excitation light having a wavelength identical to the maximum absorption length to determine the emission wavelength and the peak width at half height of the emission wavelength. The results are also shown in Table 1.

3. Pyrolysis Temperature:

Pyris 1 TGA of Perkin Elmer was used to determine the pyrolysis temperature. The temperature of each of the imidazo[1,2-a]pyrimidine-containing compounds in Examples 1-9 was raised from 50° C. to 800° C. at a rate of 10° C./min. The 5% weight loss temperature was measured, which indicates the pyrolysis temperature of each of the imidazo[1,2-a]pyrimidine-containing compounds in Examples 1-9. The results are also shown in Table 1.

TABLE 1

| | Examples | | | | | | | | |
|---|---|---|---|---|---|---|---|---|---|
| | 1 | 2 | 3 | 4 | 5 | 6 | 7 | 8 | 9 |
| UV/Vis $\lambda_{max}$ (nm) | 370 | 370 | 365 | 375 | 370 | 365 | 365 | 370 | 365 |
| PL $\lambda$max (nm) | 464 | 456 | 470 | 475 | 479 | 470 | 475 | 480 | 476 |
| Peak width at half height (nm) | 87.05 | 71.08 | 77.20 | 80.95 | 81.27 | 77.22 | 79.66 | 82.30 | 83.49 |
| Pyrolysis temperature (° C.) | 327 | 372 | 300 | 325 | 297 | 296 | 333 | 292 | 297 |

Figure 2:
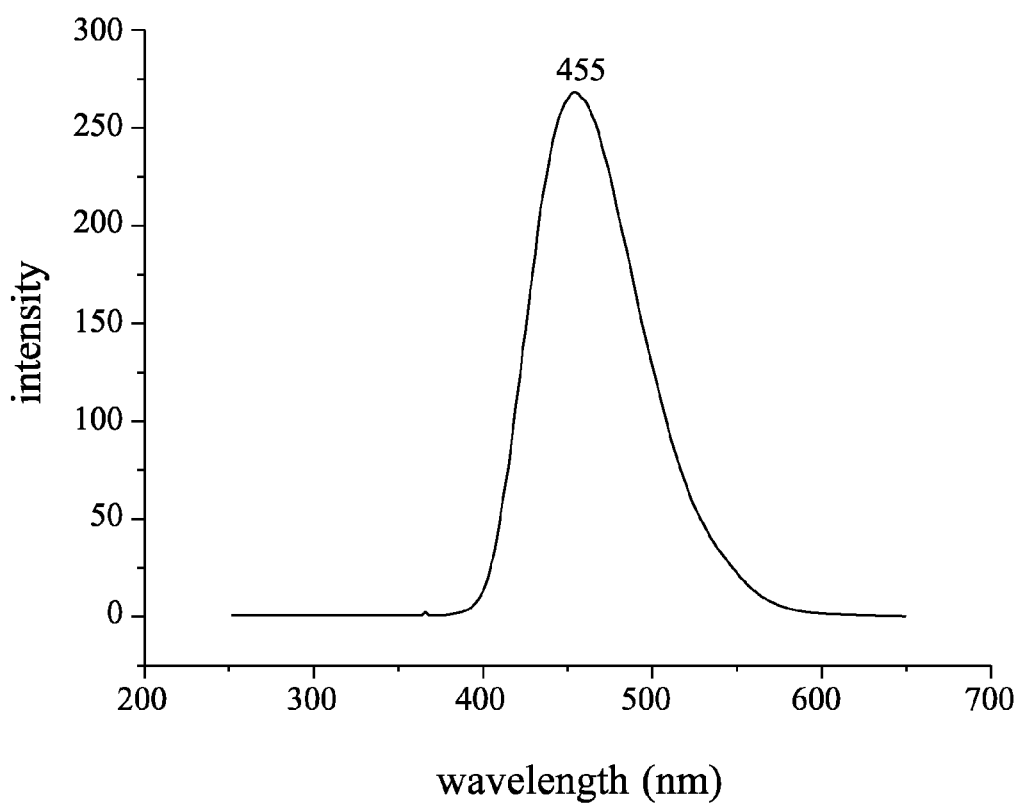
Figure 3:
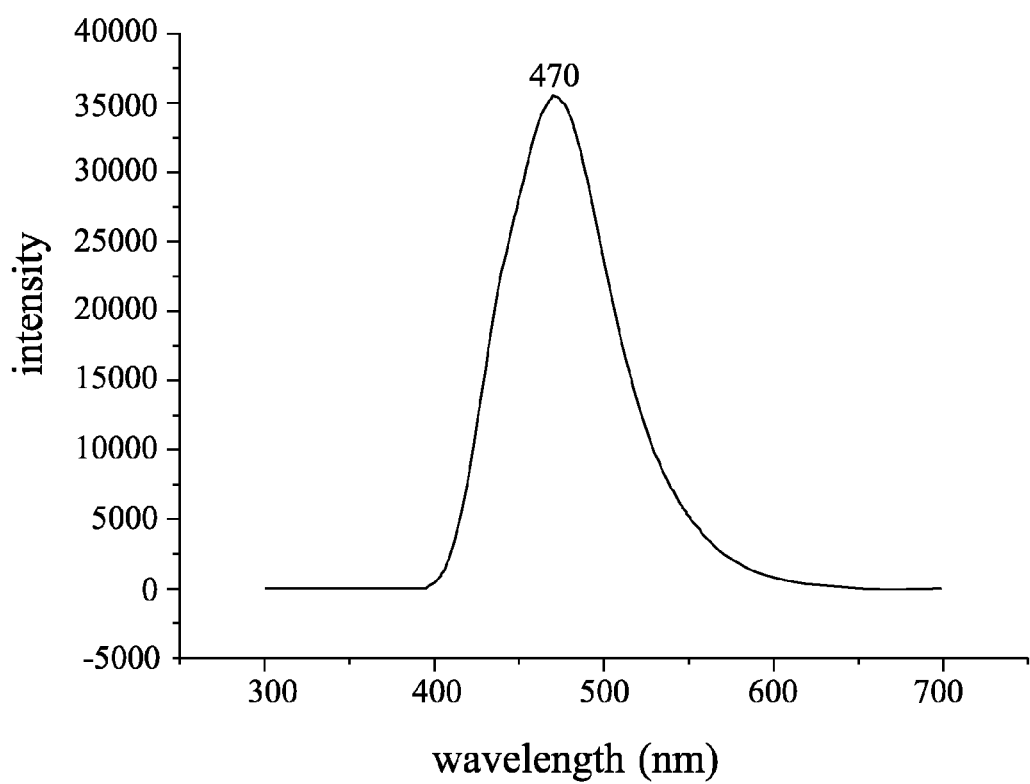
Figure 4:
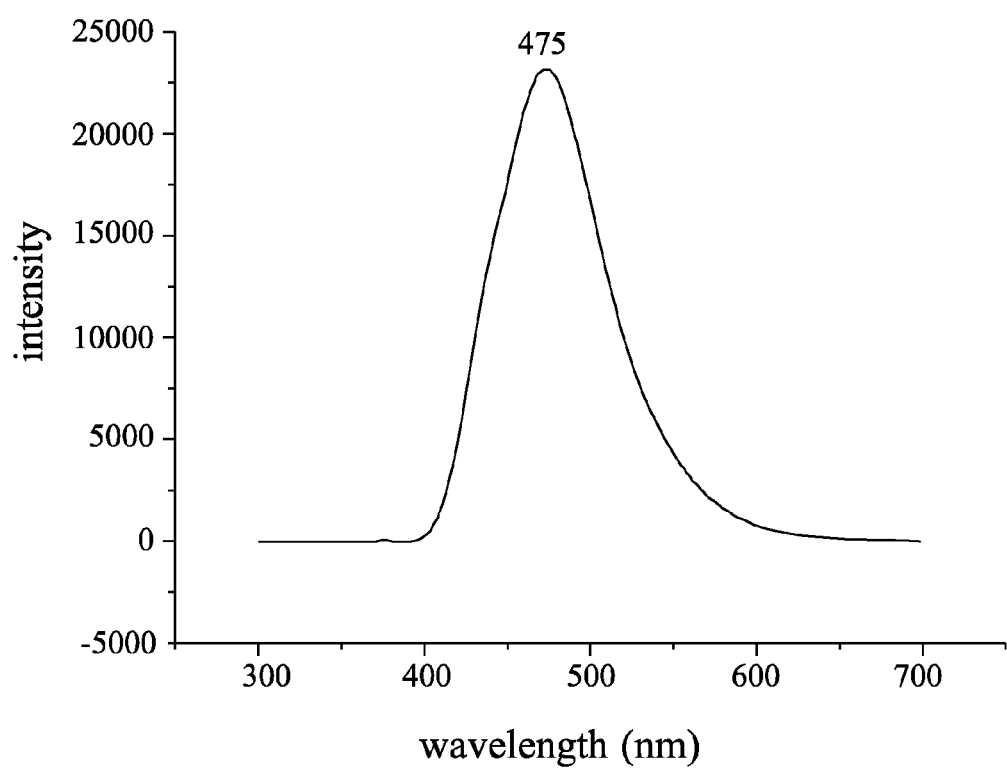
Figure 5:
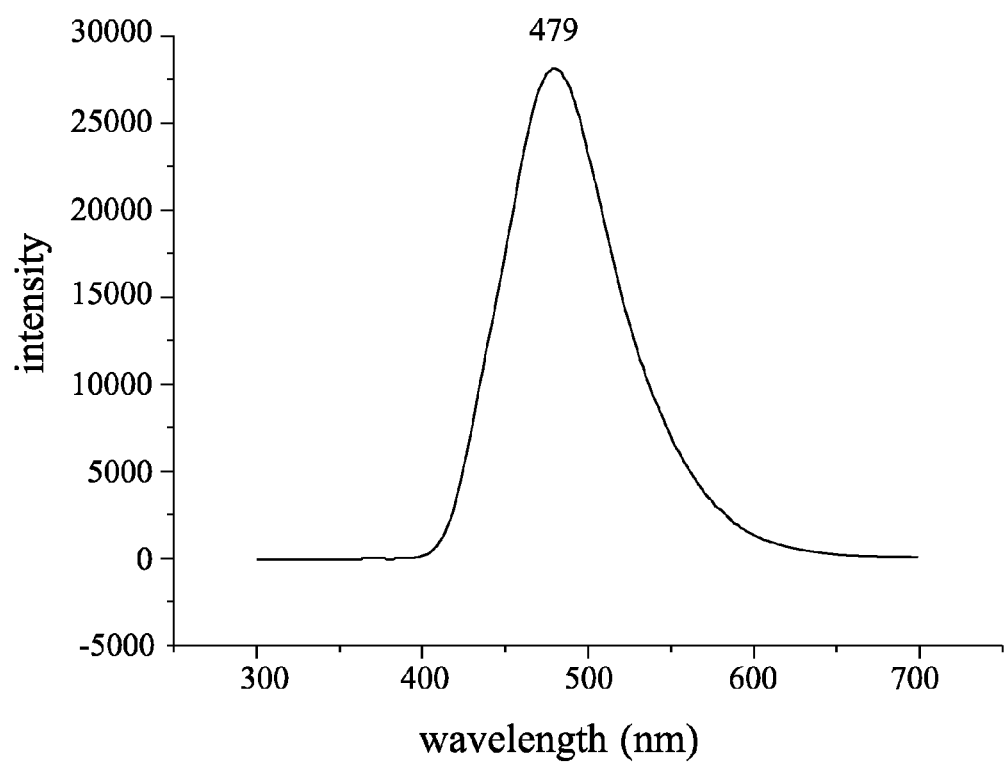
Figure 6:
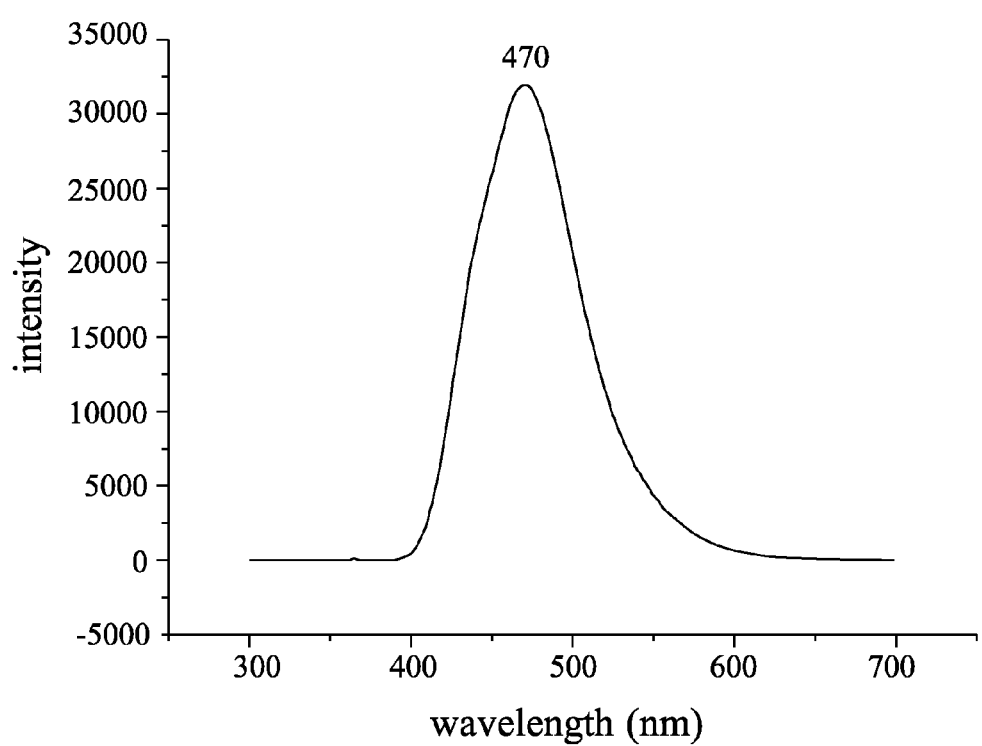
Figure 7:
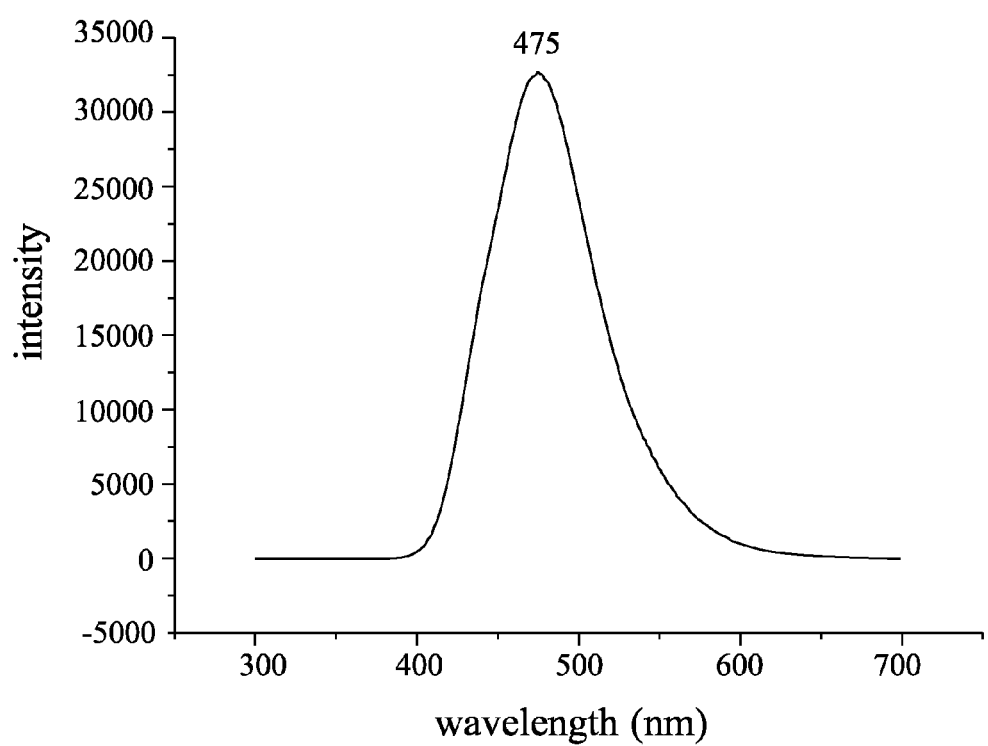
Figure 8:
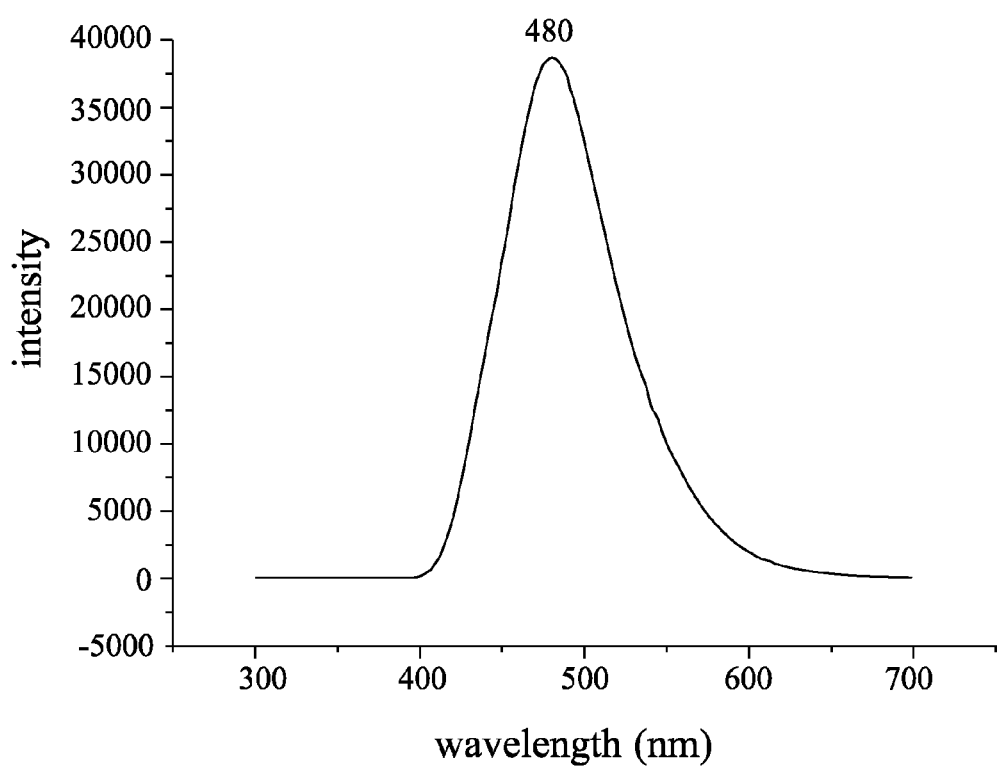
Figure 9:
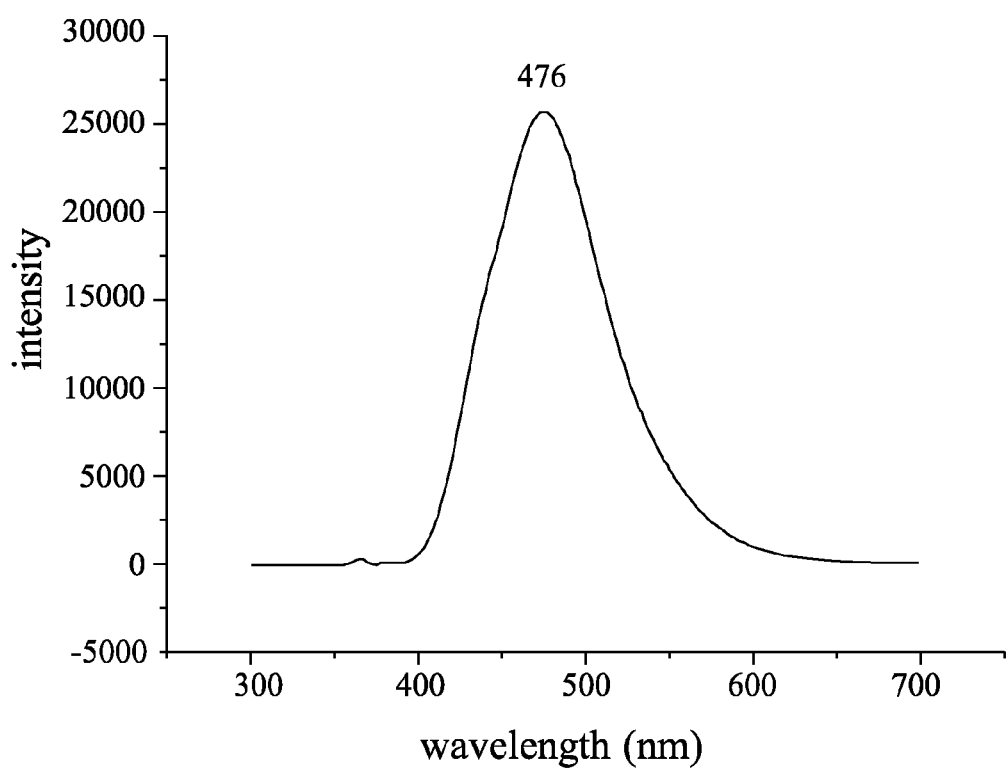

As shown in Table 1 and FIGS. 1-9, the imidazo[1,2-a]pyrimidine-containing compounds in Examples 1-9 emit blue fluorescent light having a wavelength ranging from 456 to 480 nm under photoluminescence excitation.

The imidazo[1,2-a]pyrimidine-containing compounds in Examples 1-9 have a peak width at half height ranging from 71.08 nm to 87.05 nm, which indicates the imidazo[1,2-a]pyrimidine-containing compounds emit blue fluorescent light having high color purity. The imidazo[1,2-a]pyrimidine-containing compounds obtained in Examples 1-7 and 9 have a pyrolysis temperature ranging from 296° C. to 372° C., which indicates the imidazo[1,2-a]pyrimidine-containing compounds have superior thermal stability and do not readily decompose during the gasification process. Furthermore, when used in organic light-emitting diodes, the imidazo[1,2-a]pyrimidine-containing compound of this disclosure has superior thermal stability and does not readily decompose under power-on condition. Therefore, the light-emitting efficiency of organic light-emitting diode may be enhanced.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. An imidazo[1,2-a]pyrimidine-containing compound represented by formula (I):

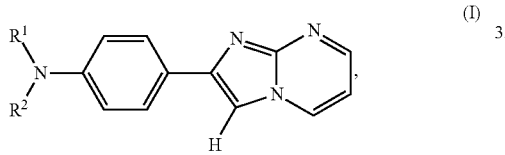

wherein
R$^1$ and R$^2$ independently represent hydrogen, an alkyl group, or an aryl group which is unsubstituted or substituted with at least one substituent selected from the group consisting of an alkyl group, an alkoxy group, and a halo group with the proviso that at least one of R$^1$ and R$^2$ is said aryl group.

2. The compound according to claim 1, wherein said compound emits blue fluorescent light under photoluminescence or electroluminescence excitation.

3. The compound according to claim 1, wherein said aryl group is selected from the group consisting of:

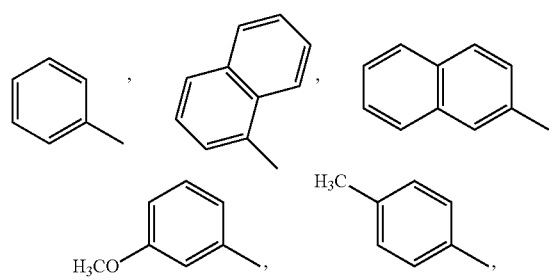

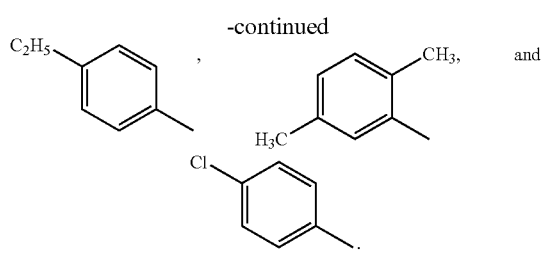

4. The compound according to claim 1, wherein said alkyl group contains from 1 to 25 carbon atoms.

5. The compound according to claim 1, wherein both R$^1$ and R$^2$ independently represent said aryl group.

6. An electronic device comprising the compound according to claim 1.

7. A method for preparing the compound according to claim 1, comprising subjecting a compound of formula (II) to an amination reaction with a compound of formula (III),

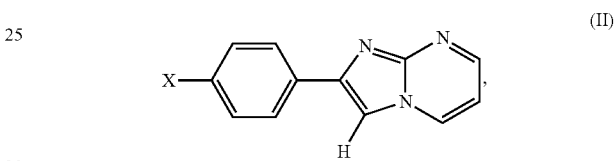

wherein X represents I, Br, F, or Cl,

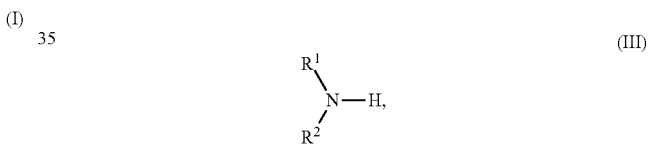

wherein R$^1$ and R$^2$ independently represent hydrogen, an alkyl group, or an aryl group which is unsubstituted or substituted with at least one substituent selected from the group consisting of an alkyl group, an alkoxy group, and a halo group with the proviso that at least one of R$^1$ and R$^2$ is said aryl group.

8. The method according to claim 7, which is performed in the presence of a catalyst and a solvent.

9. The method according to claim 7, which is performed at a temperature ranging from 110° C. to 130° C.

10. The method according to claim 7, wherein said aryl group is selected from the group consisting of:

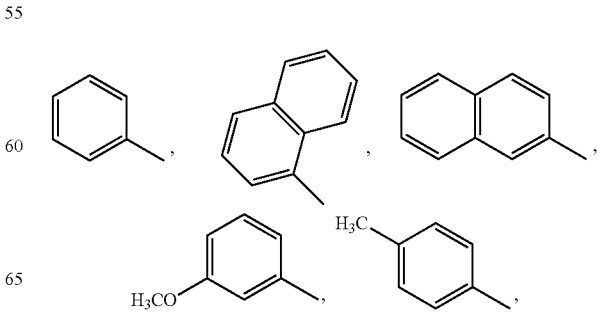

-continued

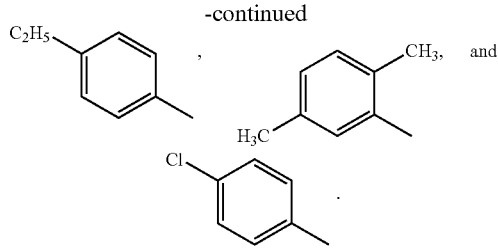

11. The method according to claim 7, wherein said alkyl group contains from 1 to 25 carbon atoms.

12. The method according to claim 11, wherein said alkyl group contains from 1 to 10 carbon atoms.

13. The method according to claim 12, wherein said alkyl group contains from 1 to 5 carbon atoms.

14. The method according to claim 7, wherein both $R^1$ and $R^2$ independently represent said aryl group.

* * * * *